(12) United States Patent
Young et al.

(10) Patent No.: US 7,979,136 B2
(45) Date of Patent: Jul. 12, 2011

(54) METHOD AND SYSTEM FOR MULTI-DEVICE COMMUNICATION

(75) Inventors: Morris J. Young, Indianapolis, IN (US); David Bradley Markisohn, Indianapolis, IN (US); Allen B. Cummings, Westfield, IN (US); Adam R. Scroggin, Noblesville, IN (US)

(73) Assignee: Roche Diagnostics Operation, Inc, Indianapolis, IN (US)

( * ) Notice: Subject to any disclaimer, the term of this patent is extended or adjusted under 35 U.S.C. 154(b) by 856 days.

(21) Appl. No.: 11/999,866

(22) Filed: Dec. 7, 2007

(65) Prior Publication Data

US 2009/0150175 A1 Jun. 11, 2009

(51) Int. Cl.
*A61N 1/00* (2006.01)
(52) U.S. Cl. .......................................... 607/60
(58) Field of Classification Search ................ 607/5, 60; 455/41.2
See application file for complete search history.

(56) References Cited

U.S. PATENT DOCUMENTS

| | | | |
|---|---|---|---|
| 4,731,726 A | 3/1988 | Allen, III | |
| 5,251,126 A | 10/1993 | Kahn et al. | |
| 5,338,157 A | 8/1994 | Blomquist | |
| 5,376,070 A | 12/1994 | Purvis et al. | |
| 5,658,250 A | 8/1997 | Blomquist et al. | |
| 5,665,065 A | 9/1997 | Colman et al. | |
| 5,795,327 A | 8/1998 | Wilson et al. | |
| 5,954,641 A | 9/1999 | Kehr et al. | |
| 6,024,699 A | 2/2000 | Surwit et al. | |
| 6,068,615 A | 5/2000 | Brown et al. | |
| 6,102,855 A | 8/2000 | Kehr et al. | |
| 6,110,148 A | 8/2000 | Brown et al. | |
| 6,113,578 A | 9/2000 | Brown | |
| 6,141,584 A * | 10/2000 | Rockwell et al. | 607/5 |
| 6,241,704 B1 | 6/2001 | Peterson et al. | |
| 6,314,405 B1 | 11/2001 | Richardson | |
| 6,322,502 B1 | 11/2001 | Schoenberg et al. | |
| 6,368,272 B1 | 4/2002 | Porumbescu | |
| 6,427,088 B1 | 7/2002 | Bowman, IV et al. | |
| 6,544,212 B2 | 4/2003 | Galley et al. | |
| 6,551,276 B1 | 4/2003 | Mann et al. | |
| 6,558,320 B1 | 5/2003 | Causey, III et al. | |
| 6,562,001 B2 | 5/2003 | Lebel et al. | |
| 6,564,105 B2 | 5/2003 | Starkweather et al. | |
| 6,571,128 B2 | 5/2003 | Lebel et al. | |
| 6,577,899 B2 | 6/2003 | Lebel et al. | |
| 6,585,644 B2 | 7/2003 | Lebel et al. | |
| 6,605,038 B1 | 8/2003 | Teller et al. | |
| 6,635,014 B2 | 10/2003 | Starkweather et al. | |
| 6,648,821 B2 | 11/2003 | Lebel et al. | |

(Continued)

FOREIGN PATENT DOCUMENTS

EP 0 699 046 9/1996

(Continued)

OTHER PUBLICATIONS

International Preliminary Report on Patentability for PCT/EP2008/009878 issued by the European Patent Office on Jun. 29, 2009 (4 pgs.).

(Continued)

*Primary Examiner* — George Manuel
(74) *Attorney, Agent, or Firm* — Baker & Daniels LLP

(57) ABSTRACT

A medical data system including a plurality of receivers configured to wirelessly receive medical data via a signal.

20 Claims, 2 Drawing Sheets

U.S. PATENT DOCUMENTS

| | | | |
|---|---|---|---|
| 6,659,948 B2 | 12/2003 | Lebel et al. | |
| 6,668,196 B1 | 12/2003 | Villegas et al. | |
| 6,687,546 B2 | 2/2004 | Lebel et al. | |
| 6,694,191 B2 | 2/2004 | Starkweather et al. | |
| 6,714,724 B1 | 3/2004 | Cook | |
| 6,733,446 B2 | 5/2004 | Lebel et al. | |
| 6,740,075 B2 | 5/2004 | Lebel et al. | |
| 6,752,787 B1 | 6/2004 | Causey, III et al. | |
| 6,758,810 B2 | 7/2004 | Lebel et al. | |
| 6,781,522 B2 | 8/2004 | Sleva et al. | |
| 6,804,656 B1 | 10/2004 | Rosenfeld et al. | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,852,104 B2 | 2/2005 | Blomquist | |
| 6,873,268 B2 | 3/2005 | Lebel et al. | |
| 6,958,705 B2 | 10/2005 | Lebel et al. | |
| 7,020,508 B2 | 3/2006 | Stivoric et al. | |
| 7,024,236 B2 | 4/2006 | Ford et al. | |
| 7,029,455 B2 | 4/2006 | Flaherty | |
| 7,039,703 B1 | 5/2006 | Clancy et al. | |
| 7,041,468 B2 | 5/2006 | Drucker et al. | |
| 7,063,665 B2 | 6/2006 | Hasegawa et al. | |
| 7,072,356 B1 | 7/2006 | Clancy et al. | |
| 7,082,334 B2 | 7/2006 | Boute et al. | |
| 7,120,488 B2 | 10/2006 | Nova et al. | |
| 7,149,474 B1 * | 12/2006 | Mikhak | 455/41.2 |
| 7,165,062 B2 | 1/2007 | O'Rourke | |
| 7,179,226 B2 | 2/2007 | Crothall et al. | |
| 7,181,350 B2 | 2/2007 | Oberding et al. | |
| 2002/0016568 A1 | 2/2002 | Lebel et al. | |
| 2002/0029776 A1 | 3/2002 | Blomquist | |
| 2002/0040208 A1 | 4/2002 | Flaherty et al. | |
| 2002/0193679 A1 | 12/2002 | Malave et al. | |
| 2003/0011646 A1 | 1/2003 | Levine et al. | |
| 2003/0060765 A1 | 3/2003 | Campbell et al. | |
| 2003/0065308 A1 | 4/2003 | Lebel et al. | |
| 2003/0065536 A1 | 4/2003 | Hansen et al. | |
| 2003/0163088 A1 | 8/2003 | Blomquist | |
| 2003/0163789 A1 | 8/2003 | Blomquist | |
| 2003/0174049 A1 | 9/2003 | Beigel et al. | |
| 2004/0073464 A1 | 4/2004 | Huang | |
| 2004/0119742 A1 | 6/2004 | Silbey et al. | |
| 2004/0172284 A1 | 9/2004 | Sullivan et al. | |
| 2004/0235446 A1 | 11/2004 | Flaherty et al. | |
| 2004/0254434 A1 | 12/2004 | Goodnow et al. | |
| 2004/0260233 A1 | 12/2004 | Garibotto et al. | |
| 2005/0004947 A1 | 1/2005 | Emlet et al. | |
| 2005/0022274 A1 | 1/2005 | Campbell et al. | |
| 2005/0059867 A1 | 3/2005 | Cheng | |
| 2005/0102167 A1 * | 5/2005 | Kapoor | 705/3 |
| 2005/0137653 A1 | 6/2005 | Friedman et al. | |
| 2005/0192844 A1 | 9/2005 | Esler et al. | |
| 2006/0025075 A1 | 2/2006 | Chung et al. | |
| 2006/0167367 A1 | 7/2006 | Stanczak et al. | |
| 2006/0248398 A1 | 11/2006 | Neel et al. | |
| 2006/0279431 A1 | 12/2006 | Bakarania et al. | |
| 2007/0033074 A1 | 2/2007 | Nitzan et al. | |
| 2007/0048691 A1 | 3/2007 | Brown | |
| 2007/0135866 A1 * | 6/2007 | Baker et al. | 607/60 |
| 2007/0179352 A1 | 8/2007 | Randlov et al. | |
| 2007/0219432 A1 | 9/2007 | Thompson | |
| 2007/0276197 A1 | 11/2007 | Harmon | |

FOREIGN PATENT DOCUMENTS

| | | |
|---|---|---|
| EP | 0 970 655 | 1/2000 |
| EP | 0 649 316 B1 | 12/2000 |
| EP | 1 194 864 A2 | 4/2002 |
| EP | 1 502 614 | 2/2005 |
| EP | 1 722 310 | 4/2005 |
| EP | 1 758 039 | 2/2007 |
| WO | WO9728736 | 2/1997 |
| WO | WO9935856 | 12/1998 |
| WO | WO0018449 | 2/2000 |
| WO | WO0072181 | 11/2000 |
| WO | WO0200111 | 1/2002 |
| WO | WO02078512 | 10/2002 |
| WO | WO03015838 | 2/2003 |
| WO | WO2004090661 | 10/2004 |
| WO | WO2005011249 | 2/2005 |
| WO | WO2005037095 | 4/2005 |
| WO | WO2005096206 | 10/2005 |
| WO | WO2005114534 | 12/2005 |
| WO | WO2005114535 | 12/2005 |
| WO | WO2006050485 | 2/2006 |
| WO | WO2006108858 | 10/2006 |
| WO | WO2006118763 | 11/2006 |
| WO | WO2007051139 | 5/2007 |
| WO | WO2007093482 | 8/2007 |
| WO | WO2008147567 | 12/2008 |

OTHER PUBLICATIONS

Cabri et al.; "Agent-based Plug-and-Play Integration of Role-Enabled Medical Devices", IEEE Computer Society, Aug. 2007, p. 111-121.

"The HAVi Specification—Specification of the Home Audio/Video Interoperability (HAVi) Architecture," Nov. 19, 1998, pp. 1-409, Version 1.0 beta.

Hotchkiss et al.; "MD-Adapt a Proposed Architecture for Open-Source Medical Device Interoperability", 2007, IEEE Computer Society, Aug. 2007, pp. 167-169.

"CoPilot Health Management System Version 3.1," Users Guide, Mar. 2007, 230 pp., ART 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software is an Effective Tool for the Management of Diabetes," Bayer HealthCare Clinical Summary Report, Jul. 2005, 10 pp.

Joshy et al.; "Diabetes Information Systems: A Rapidly Emerging Support for Diabetes Surveillance and Care," Diabetes Technology & Therapeutics, 2006, pp. 587-597, vol. 8, No. 5.

"OneTouch Diabetes Management Software," User Manual, 2006, 173 pp., v. 2.3.1, Lifescan, Inc.

"Getting Started, CareLink Personal Therapy Management Software for Diabetes," Brochure, 2007, 20 pp., Medtronic Minimed, Inc.

"Accu-Chek® Camit Pro Diabetes Management Software," User's Manual, 2005, 220 pp., v.2.1 and Addendum v. 2.4, Roche Diagnostics Corp.

"Accu-Chek® Compass Diabetes Care Software," User's Guide, 2005, 74 pp., Roche Diagnostics Corp.

"Accu-Chek® Diabetes Assistant," accessed with notional data and printed from www.diabetesassistant.com on Jan. 16, 2007, 20 pp., Roche Diagnostics Corp.

* cited by examiner

METHOD AND SYSTEM FOR MULTI-DEVICE COMMUNICATION

FIELD OF THE INVENTION

The present disclosure relates to a method and system for managing health data. More particularly, the disclosure relates a method and system for interfacing with a medical device.

BACKGROUND

Many fields of medical treatment and healthcare require monitoring of certain body functions, physical states and conditions, and patient behaviors. Thus, e.g., for patients suffering from diabetes, a regular check of the blood glucose level forms an essential part of the daily routine. The blood glucose level has to be determined quickly and reliably, often several times per day. Medical devices are used to facilitate the collection of medical information without unduly disturbing the lifestyle of the patient. A large number of medical devices for monitoring various body functions are commercially available. Also, medical treatment and healthcare may require monitoring of exercise, diet, meal times, stress, work schedules and other activities and behaviors.

To reduce the frequency of necessary visits to doctors, the idea of home care gained popularity over the recent years. Technological advancements in medicine led to the increased use of medical devices. Many of these medical devices, such as meters and medicine delivery devices, are able to collect and store measurements and other data for long periods of time. Other devices, such as computers, portable digital assistants (PDAs), and cell phones, have been adapted to medical uses by the development of software directed to the collection of healthcare data. These advancements led to the development of health management systems that enable collection and use of large numbers of variables and large amounts of healthcare data. While systems were traditionally developed for use in healthcare facilities and health management organizations including insurance companies and governmental agencies (HCP systems), increased technological sophistication by the populous at large led to the increased use of health management systems by patients, care givers, and others (patient systems) in addition to increased use by HCP systems. U.S. Pat. No. 7,103,578 and U.S. Published Application No. 2004/0172284 disclose two such methods and systems. Many of these systems are able to transfer data between them.

SUMMARY

The disclosure relates to a method and system for interfacing between a healthcare management system and medical devices. One embodiment of the system includes a medical data transmission system including a first dongle coupled to a first computing entity and configured to wirelessly receive medical data via a signal generated by a first medical device; and a second dongle coupled to the first computing entity and configured to wirelessly receive medical data via a signal generated by a second medical device; the second dongle being configured to wirelessly receive medical data simultaneously with the first dongle wirelessly receiving medical data.

In another embodiment, a computer readable medium is provided. The computer readable medium including operating instructions thereon such that when interpreted by a processor cause the processor to perform the step of simultaneously wirelessly downloading medical information from a first and second medical data devices.

In another embodiment, a medical data transmission system is provided. The system including a first transceiver configured to wirelessly receive medical data from a first medical device via a first data signal; the first transceiver emitting a first beacon signal detectable by the first medical device, and a second transceiver configured to wirelessly receive medical data from a second medical device via a second data signal; the second transceiver emitting a second beacon signal detectable by the second medical device.

DESCRIPTION OF THE DRAWINGS

For more complete understanding of the present disclosure, reference is established to the following drawings in which.

Figure 1:
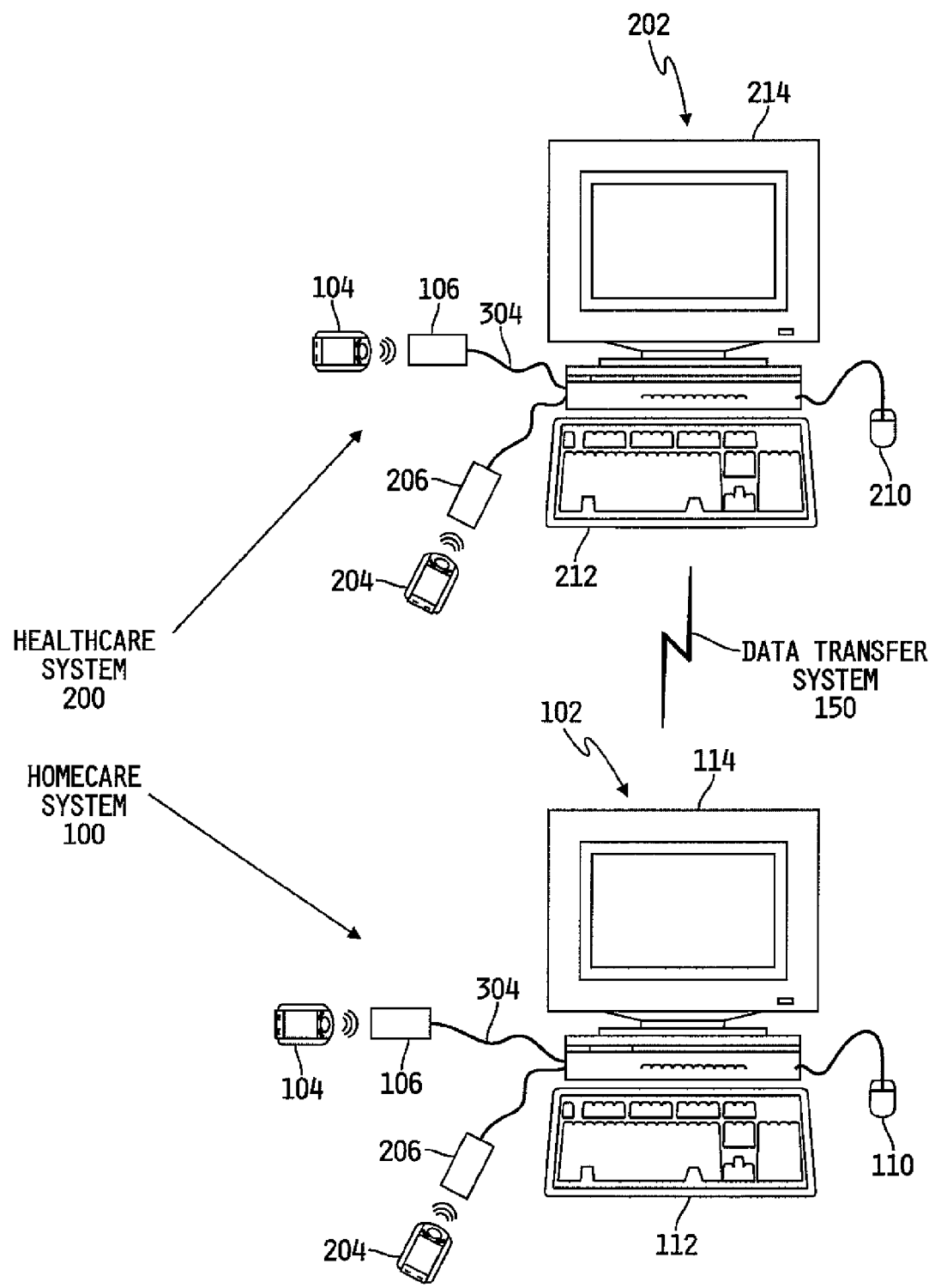
FIG. 1 shows an embodiment of a health management system comprising a healthcare system and a homecare system.

Corresponding reference characters indicate corresponding parts throughout the several views. Although the drawings represent embodiments of various features and components according to the present invention, the drawings are not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION OF EMBODIMENTS OF THE INVENTION

For the purposes of promoting an understanding of the principles of the disclosure, reference will now be made to the embodiments illustrated in the drawings, which are described below. The embodiments disclosed below are not intended to be exhaustive or limit the disclosure to the precise form disclosed in the following detailed description. Rather, the embodiments are chosen and described so that others skilled in the art may utilize their teachings. It will be understood that no limitation of the scope of the invention is thereby intended. The disclosure includes any alterations and further modifications in the illustrated devices and described methods and further applications of the principles of the disclosure which would normally occur to one skilled in the art to which the disclosure relates.

Concepts described below may be further explained in one of more of the co-filed patent applications entitled HELP UTILITY FUNCTIONALITY AND ARCHITECTURE Ser. No. 11/999,906, METHOD AND SYSTEM FOR GRAPHICALLY INDICATING MULTIPLE DATA VALUES Ser. No. 11/999,853, SYSTEM AND METHOD FOR DATABASE INTEGRITY CHECKING Ser. No. 11/999,856, METHOD AND SYSTEM FOR DATA SOURCE AND MODIFICATION TRACKING Ser. No. 11/999,888, PATIENT-CENTRIC HEALTHCARE INFORMATION MAINTENANCE Ser. No. 11/999,874, EXPORT FILE FORMAT WITH MANIFEST FOR ENHANCED DATA TRANSFER Ser. No. 11/999,867, GRAPHIC ZOOM FUNCTIONALITY FOR A CUSTOM REPORT Ser. No. 11/999,932, METHOD AND SYSTEM FOR SELECTIVE MERGING OF PATIENT DATA Ser. No. 11/999,859, METHOD AND SYSTEM FOR PERSONAL MEDICAL DATA DATABASE MERGING Ser. No. 11/999,772, METHOD AND SYSTEM FOR WIRELESS DEVICE COMMUNICATION Ser. No. 11/999,879, METHOD AND SYSTEM FOR SETTING TIME BLOCKS Ser. No. 11/999,968, METHOD AND SYSTEM FOR ENHANCED DATA TRANSFER Ser. No. 11/999,911, COMMON EXTENSIBLE DATA EXCHANGE FORMAT Ser. No. 11/999,871, METHOD OF CLONING SERVER INSTALLATION TO A NETWORK CLIENT Ser. No. 11/999,876, METHOD AND SYSTEM FOR QUERYING A DATABASE Ser. No. 11/999,912, METHOD AND SYSTEM FOR EVENT BASED DATA COMPARISON Ser. No. 11/999,921, DYNAMIC COMMUNICATION STACK Ser. No. 11/999,934, SYSTEM AND METHOD FOR REPORTING MEDICAL INFORMATION Ser. No. 11/999,878, METHOD AND SYSTEM FOR MERGING EXTENSIBLE DATA INTO A DATABASE USING GLOBALLY UNIQUE IDENTIFIERS Ser. No. 11/999,947, METHOD AND SYSTEM FOR ACTIVATING FEATURES AND FUNCTIONS OF A CONSOLIDATED SOFTWARE APPLICATION Ser. No. 11/999,880, METHOD AND SYSTEM FOR CONFIGURING A CONSOLIDATED SOFTWARE APPLICATION Ser. No. 11/999,894, METHOD AND SYSTEM FOR DATA SELECTION AND DISPLAY Ser. No. 11/999,896, METHOD AND SYSTEM FOR ASSOCIATING DATABASE CONTENT FOR SECURITY ENHANCEMENT Ser. No. 11/999,951, METHOD AND SYSTEM FOR CREATING REPORTS Ser. No. 11/999,851, METHOD AND SYSTEM FOR CREATING USER-DEFINED OUTPUTS Ser. No. 11/999,905, DATA DRIVEN COMMUNICATION PROTOCOL GRAMMAR Ser. No. 11/999,770, and HEALTHCARE MANAGEMENT SYSTEM HAVING IMPROVED PRINTING OF DISPLAY SCREEN INFORMATION Ser. No. 11/999,855, the entire disclosures of which are hereby expressly incorporated herein by reference. It should be understood that the concepts described below may relate to diabetes management software systems for tracking and analyzing health data, such as, for example, the Accu-Chek® 360○ product provided by Roche Diagnostics. However, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the Accu-Chek® Active, Accu-Chek® Aviva, Accu-Chek® Compact, Accu-Chek® Compact Plus, Accu-Chek® Integra, Accu-Chek® Go, Accu-Chek® Performa, Accu-Chek® Spirit, Accu-Chek® D-Tron Plus, and Accu-Chek® Voicemate Plus, all provided by Roche Diagnostics or divisions thereof.

The terms "network," "local area network," "LAN," "wide area network," or "WAN" mean two or more computers which are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks can access the network resources, such as shared data files, common peripheral devices, and inter-workstation communication. The computers have at least one processor for executing machine instructions, and memory for storing instructions and other information. Many combinations of processing circuitry and information storing equipment are known by those of ordinary skill in these arts. A processor may be a microprocessor, a digital signal processor ("DSP"), a central processing unit ("CPU"), or other circuit or equivalent capable of interpreting instructions or performing logical actions on information. Memory includes both volatile and non-volatile memory, including temporary and cache, in electronic, magnetic, optical, printed, or other format used to store information. Users activate computer programs or network resources to create "processes" which include both the general operation of the computer program along with specific operating characteristics determined by input variables and its environment.

Turning now to the figures, FIG. 1 depicts an exemplary embodiment of a homecare system 100 and healthcare system 200 connected via a WAN 150 for monitoring data. Systems 100, 200 each comprise a computing device, shown here in the form of computers 102, 202 having processing units, system memory, display devices 114, 214, and input devices 112, 212, 110, 210, 106, 206. Healthcare computer 202 may be, but is not necessarily, acting as a server. Likewise, homecare computer 102 may be, but is not necessarily, acting as a client. Furthermore, while only two computers 102, 202 are shown, many more computers may be part of the overall system.

While standard input devices such as mice 110, 210 and keyboards 112, 212 are shown, systems 100, 200 may comprise any user input device. By example, infrared (IR) dongles 106, 206 are coupled to each of computers 102, 202. IR dongles 106, 206 are configured to send and receive IR transmissions from health management devices 104, 204. Computers 102, 202 include software applications configured to receive data from health management devices 104, 204 via IR dongles 106, 206 or otherwise. While the use of IR and IR dongles 106, 206 is disclosed herein for the transmission of data between health management devices 104, 204 and computers 102, 202, any other method of wireless transmission is also envisioned, including but not limited to RF. Systems 100, 200 include health management software (not shown) configured to receive medical information from one or more of input devices 112, 212, 110, 210, 106, 206. Health management devices 104, 204 are described herein as meters, but could also be PDA's, therapeutic pumps, combinations thereof, or other devices that store medical data thereon. Medical information may include blood glucose values, A1c values, Albumin values, Albumin excretion values, body mass index values, blood pressure values, carbohydrate values, cholesterol values (total, HDL, LDL, ratio) creatinine values, fructosamine values, HbA1 values, height values, insulin dose values, insulin rate values, total daily insulin values, ketone values, microalbumin values, proteinuria values, heart rate values, temperature values, triglyceride values, weight values, and any other medical information that is desired to be known.

Figure 2:
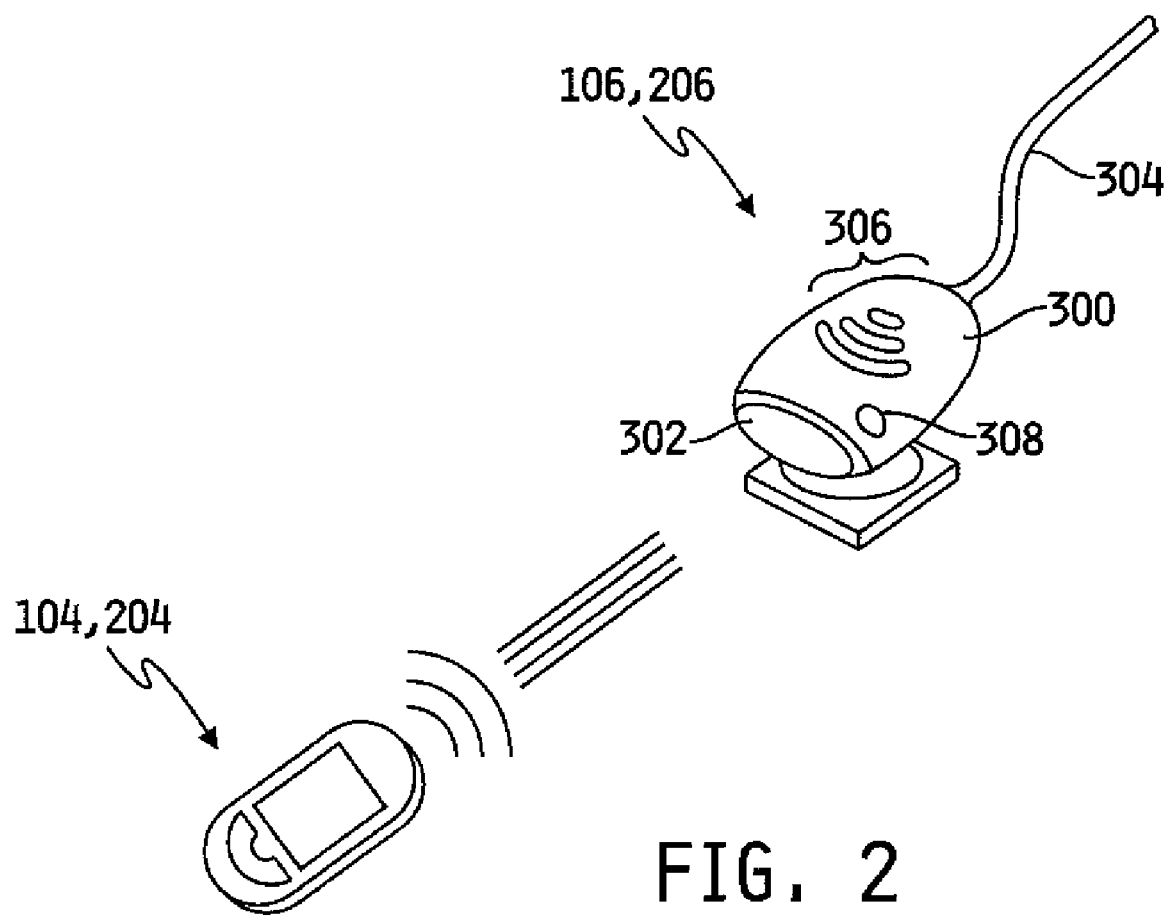
FIG. 2 is a perspective view of a dongle that is part of the systems of FIG. 1.

IR dongle 106, 206, shown in FIG. 2, includes housing 300, IR transmission window 302, and interface cable 304. Housing 300 is sized and shaped to contain IR producing and receiving circuitry therein. IR transmission window 302 is disposed on one side of housing 300 and allows the transmission of IR signals therethrough. Interface cable 304, shown as a USB cable, allows IR dongle 106, 206 to functionally couple to computers 102, 202. Housing 300 also includes reception indicator 306 and communication indicator 308 thereon. Reception indicator 306 provides an indication of reception and the strength of the signal being received from any health management device 104 within range. Reception indicator 306 further allows a user to adjust the positioning of health management device 104, 204 and receive feedback, such as, for example, the display of more or fewer reception "bars," to effect suitable positioning for data transfer. Communication indicator 308 provides an indication of when data is being transmitted between IR dongle 106, 206 and health management device 104, 204.

Health management device 104, 204 may include a housing having an IR window, an "IR detected" LED, and a "good link" LED. IR window of health management device 104, 204 is similar to the IR transmission window 302 and permits transmission of IR signals therethrough. The "IR detected" LED is similar to reception indicator 306 and provides an indication of whether a compatible dongle 106, 206 is detected within range. The "good link" LED is similar to communication indicator 308 and indicates that the IR signal from dongle 106, 206 is suitable for sustaining or is transacting data transfer. While indicators 306, 308 and the LED indicators are described as being present on both dongle 106, 206 and health management device 104, 204, embodiments are envisioned wherein indicators would only be present on one of dongle 106, 206 and health management device 104, 204.

In use, dongle 106, 206, when not transmitting data, emits a beacon. The beacon is a repetitive link command that is sent out until either a successful IR link is established with health management device 104, 204 or the software running on computer 102, 202 is shut down. Although the software is described herein for operation on computer 102, 202 (e.g., desktop, laptop or tablet), it should be understood that the principles of the invention may be embodied in software for operation on various devices, including but not limited to personal digital assistants ("PDAs"), infusion pumps, blood glucose meters, cellular phones, or integrated devices including a glucose measurement engine and a PDA or cellular device. Furthermore, dongle 106, 206 may have an instance of the software running on itself. Dongle 106, 206 may be integrated into computer 102, 202 or any other device.

Whenever health management device 104, 204 is turned on and not transmitting with dongle 106, 206, the IR communication portion of health management device 104, 204 is in a listening mode. Health management device 104, 204 is listening for the beacon from dongle 106, 206. Listening mode is a mode of reduced power draw relative to a data transmission mode to prolong battery life while still being able to detect dongle 106, 206. Listening involves periodic scanning for or otherwise attempting to sense the presence of the beacon. Upon "hearing" the beacon, health management device 104, 204 recognizes the beacon and wakes up to an active state. Transition from listening mode to the active state in one present embodiment of the invention takes less than five seconds. Health management device 104, 204 then emits data necessary for a handshaking protocol in which health management device 104, 204 and dongle 106, 206 exchange data to ensure that a proper device 104, 106, 204, 206 is on the receiving end of their respective transmissions, to ensure that the other device is prepared to communicate, and to coordinate the start of data transfer.

Once handshaking indicates that proper devices are present, health management device 104, 204 commences sharing any information that is desired to be shared with dongle 106, 206. When the data exchange is being effected, communication indicator 308 and the "good link" LED are illuminated to indicate that a proper link has been established. Accordingly, a user is provided with visual feedback that health management device 104, 204 is suitably positioned and that data transfer is occurring. When a user sees communication indicator 308 and/or the "good link" LED turn off, the user knows that communication has completed and that health management device 104, 204 can be moved away from dongle 106, 206 without fear that such moving will negatively impact data transmission. Embodiments are envisioned where communication indicator 308 and the "good link" LED flash as data is exchanged.

During all times that the beacon is received by health management device 104, 204, the "IR detected" LED is illuminated. During all times that dongle 106, 206 detects health management device 104, 204, reception indicator 306 is illuminated. Reception indicator 306 includes the illumination of one or more "bars" or other intensity indicators to indicate the strength of the received signal. A greater number of illuminated bars indicates a stronger signal. Similarly, the "IR detected" LED can illuminate in more than one color. Red illumination of the "IR detected" LED indicates a poor signal. Yellow illumination of the LED indicates a medium strength signal. Green illumination of the LED indicates a high strength signal. Alternatively, the LED may be binary such that there is only one illumination color. In such embodiments, illumination indicates a satisfactory signal and a lack of illumination indicates a lack of a satisfactory signal. Suitable location of health management device 104, 204 in the present embodiment includes line of sight positioning such that IR signals can travel between health management device 104. 204 and dongle 106, 206 via IR transmission window 302 and the IR window of device 104, 204. Embodiments are also envisioned where instead of, or along with, visual indices 308, 306, audio indices are provided. Such audio indices could be, for example, a first beep to indicate the start of data transmission, multiple beeps to indicate completion of data transmission, and multiple beeps that change in frequency to indicate the strength of signal being received. Such audio indices provide the functionality of visual indices 308, 306 to visually impaired users. Similarly, other sensory indicators (e.g., vibration) are envisioned.

Software runs on computers 102, 202 and waits for detection of health management device 104, 204 via dongle 106, 206. The software includes a first module that is loaded automatically on startup and runs in the background to operate dongle 106, 206 and receive indications of the presence of health management device 104, 204. For each computing device on which the first module is running, the first module simultaneously scans the ports the computing device looking for dongles 106, 206. In addition to being able to support multiple dongles 106, 206, multiple dongles 106, 206 can be simultaneously discovered by the first module.

Upon detection of health management device 104, 204, the first module invokes a related second module that is suitable for receiving and displaying data therefrom. The second module either automatically accepts and downloads data from health management device 104, 204 or it prompts a user to ask if data from health management device 104, 204 should be downloaded. In embodiments where the data is automatically downloaded, it should be appreciated that such downloading occurs without any user interaction with computers 102, 202. In this automatic embodiment, the first module is loaded automatically on startup of computers 102, 202 and downloading occurs upon detection of health management device 104, 204. Thus, downloading from health management device 104, 204 is effected with zero manipulation of and zero input to (e.g., zero "clicks" of a mouse) computers 102, 202, provided they are running. In another embodiment, the first module may be configured to request user authorization/verification of the pending download of data (e.g., via a single "click" of a mouse). The second module can also be configured such that reports of the newly downloaded data are presented automatically. Accordingly, computers 102, 202 are able to produce reports with zero clicks and zero interaction with input devices 110, 112, 210, 212. In addition to zero-click downloads to computers 102, 202, downloads may be similarly performed to other devices such as printers, faxes, or e-mail messages. Output devices such as printers and faxes may be configured to automatically produce a hard-copy or report of the downloaded data.

Once first health management device 104 is detected by, for example, first dongle 106, the first module continues to scan for additional (second) health management device 204 via second dongle 206 or via dongle 106 if dongle 106 is able to support multiple devices 104, 204. Upon detection of second health management device 204, the handshaking occurs and the second software module either automatically accepts and downloads data from health management device 204 or it prompts a user to ask if data from health management device 204 should be downloaded. Accordingly, a plurality of health management devices 104, 204 can simultaneously interface with the software. Furthermore, while the detection of health management devices 104, 204 has been described in a serial fashion, the software searches all attached dongles 106, 206 simultaneously and is able to effect interfacing with multiple health management devices 104, 204 in parallel.

More specifically, when the first module is active, a Connect application programming interface (Connect API) is used. The Connect API scans all supported and utilized transports, such as dongles 106, 206, in parallel in order to search for connected devices. When the Connect API is called, a Connect package is responsible for determining all of the available transports on which to scan for a device. After doing so, each transport is searched in parallel for devices.

A Device Scan List determines the search order. The Device Scan List is composed of multiple search contexts. Each context is used to detect a different type of device. For example, a RocheACContext detects Active-Compact meters, RocheMeterContext detects all Roche meters, and RocheSpiritContext detects the Spirit pump. At run time, only one context is active at any given instance. The Device Search Order Scan List determines the order in which the contexts attempt to detect a device. If the context fails to detect anything, the next context is attempted. Each context creates and configures a protocol stack and triggers a discovery event for a found compatible device 104, 204.

As devices 104, 204 are detected, information is retrieved from each device 104, 204 (e.g., serial number, model number, device name). If the transport, for example dongle 106, on which device 104 is detected can support more than one connecting device 104, 204 then the Connect Package continues scanning dongle 106, otherwise, the scanning process is halted on dongle 106 and continued on other connected dongles 206.

As devices 104, 204 are found, an interface to them is returned to the requesting application. This interface can be used to send commands to device 104, 204 in a common application protocol. When a command is sent to device 104, 204 it is translated from the software command to device-specific command as it is passed through layers of the related protocol stack.

Once connected, data can be downloaded from the connected device 104, 204 and stored in a database within one or both of homecare system 100 and healthcare system 200. While the present disclosure has shown computers 102, 202 having only first and second dongles 106, 206, it should be appreciated that embodiments are envisioned with more than two dongles 106, 206.

Additionally, while this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A medical data transmission system including:
    a first transceiver coupled to a first computing entity at a first port and configured to detect the presence of and wirelessly receive data via a signal generated by a first medical device;
    a second transceiver coupled to the first computing entity at a second port and configured to detect the presence of and wirelessly receive data from a second medical device; and
    software running on the first computing device, the software including a first module that simultaneously scans the ports to determine whether the transceivers have detected a medical device and a second module automatically invoked by the first module when a transceiver has detected a medical device, the second module being configured to execute one of automatic downloading of patient related medical data from the detected medical device and prompting a user to authorize downloading of patient related medical data from the detected medical device.

2. The system of claim 1, wherein the first transceiver is a first dongle and the second transceiver is a second dongle.

3. The system of claim 2, wherein at least one of the first and second dongles includes an externally perceptible indicator of strength of a signal generated by a detected medical device.

4. The system of claim 3, wherein the indicator includes a set of intensity indicators such that a greater number of activated intensity indicators indicates a greater signal strength than a signal strength indicated by a smaller number of activated intensity indicators.

5. The system of claim 2, wherein at least one of the first and second dongles further includes an externally perceptible indicator of data transmission.

6. The system of claim 5, wherein the indicator of data transmission is activated concurrently with the data transmission.

7. The system of claim 1, further including a processor within the first computing entity configured to execute the first and second modules to effect automatic data transfer when one of the transceivers detects a signal from a medical device of sufficient strength for data transfer.

8. The system of claim 2, wherein at least one of the first and second dongles includes an emitter that emits a beacon to be detected by at least one of the first and second medical devices thereby causing the at least one medical device to engage in a handshaking operation with the dongle that is emitting the detected beacon.

9. A medical data transmission system including:
    a first dongle integrated into a first medical device and coupled to a first computing entity configured to wirelessly receive data via a signal generated by the first medical device, the first medical device having a glucose measurement engine therein; and
    a second dongle coupled to the first computing entity configured to wirelessly receive data via a signal generated by a second medical device; the second dongle being configured to wirelessly receive data simultaneously with the first dongle wirelessly receiving data.

10. A computer readable medium having computer executable instructions for activating an application programming interface that scans in parallel a plurality of ports of a computing device configured to couple to a plurality of transceivers for detecting and wirelessly receiving medical data from any of a plurality of medical devices within range of at least one of the plurality of transceivers, automatically simultaneously downloading patient medical data from at least two medical devices each within range of a respective at least one of the plurality of transceivers, and prompting a user to authorize downloading of the medical data when a medical device is within range of at least one of the plurality of transceivers.

11. The computer readable medium of claim 10, wherein the instructions for automatically downloading the medical data further include instructions for storing the medical data in a database, transferring the medical data to another device, and creating a report including the medical data.

12. The computer readable medium of claim 10, further including instructions for causing the plurality of transceivers to emit beacons for reception by the medical devices to initiate communication between the medical devices and the transceivers.

13. The computer readable medium of claim 12, wherein the transceivers are dongles coupled to the computing device and the ports are USB ports.

14. The computer readable medium of claim 10, further including instructions for
providing an indication of signal strength of a signal received from a detected medical device.

15. The computer readable medium of claim 10, further including instructions for
providing an indication to a user of data transfer from a detected medical device to a transceiver.

16. A medical data transmission system including:
a first transceiver configured to detect the presence of and wirelessly receive medical data from a first medical device via a first data signal; the first transceiver emitting a first beacon signal detectable by the first medical device,
a second transceiver configured to detect the presence of and wirelessly receive medical data from a second medical device via a second data signal; the second transceiver emitting a second beacon signal detectable by the second medical device, and
a computing device coupled to the first and second transceivers via a first port and a second port, respectively, the computing device executing software including a first module that simultaneously scans the ports to determine whether the transceivers have detected a medical device and a second module invoked by the first module when a transceiver has detected a medical device, the second module being configured to execute one of automatic downloading of data from the detected medical device and prompting a user to authorize downloading of data from the detected medical device.

17. The system of claim 16, wherein the beacon signals, when received by a medical device causes the medical device to enter an active state.

18. The system of claim 16, wherein the first transceiver is configured to wirelessly receive medical data from the second medical device via the second data signal; the first beacon signal being detectable by the second medical device.

19. The system of claim 18, wherein each of the first and second medical devices have a listening mode of decreased power consumption relative to an active state.

20. A medical data communication system, comprising:
a plurality of healthcare management devices capable of generating, storing, and communicating medical information including at least one of blood glucose values, A1c values, Albumin values, Albumin excretion values, body mass index values, blood pressure values, carbohydrate values, cholesterol values, creatinine values, fructosamine values, HbA1 values, height values, insulin dose values, insulin rate values, total daily insulin values, ketone values, microalbumin values, proteinuria values, heart rate values, temperature values, triglyceride values, and weight values, the plurality of healthcare management devices each having a housing, an infrared transmission window, a machine executable program, a light-emitting diode indicator configured to indicate the detection of an infrared dongle compatible with the machine executable program of the healthcare management device, wherein the machine executable program includes a plurality of modes including a noncommunication mode configured to execute when the healthcare management device is not in communication with an infrared dongle and an active mode configured to execute upon the healthcare management device communicating with an infrared dongle, further wherein the healthcare management device is configured to initiate a handshake protocol when an infrared dongle compatible with the machine executable program of the healthcare management device is recognized and upon completion of the handshake protocol the healthcare management device is configured to communicate the generated medical information to the infrared dongle;
a computing device, including a display, a plurality of universal serial bus ports configured to receive universal serial bus interface cables, a memory capable of receiving and storing medical information and having a machine readable program with a first module and a second module, and a processor configured to execute the machine readable program of the memory, wherein the first module includes a plurality of machine executable instructions configured to operate independently of the display and configured to scan the plurality of universal serial bus ports for detection of a state of connectivity of at least one of the plurality of healthcare management devices and upon detection of the state of connectivity the first module being configured to invoke the second module having a second plurality of machine executable instructions capable of downloading the medical information generated and stored in the at least one of the plurality of healthcare management devices, wherein the second module is capable of automatically downloading the medical information generated and stored in the at least one of the plurality of healthcare management devices and downloading the medical information generated and stored in the at least one of the plurality of healthcare management devices upon execution of a user command, and further wherein the computing device is capable of communication with a wireless network; and
a plurality of infrared dongles each having a housing, an infrared transmission window configured for transmitting and receiving infrared transmissions from the plurality of healthcare management devices, a reception indicator having a plurality of reception bar indices and configured to indicate the communication ability of the infrared dongle with a detected healthcare management device, a communication indicator configured to indicate communication of medical information from a healthcare management device to the infrared dongle, and an emitter capable of repeatedly transmitting an infrared communication beacon, wherein the infrared communication beacon is configured to be detectable by a compatible healthcare management device and elicit an infrared transmission response from the healthcare management device, further wherein each infrared dongle of the plurality of infrared dongles is capable of connecting to a universal serial bus cable such that each infrared dongle is capable of coupling to a computing device at one of the plurality of universal serial bus ports of the computing device, and further wherein each infrared dongle of the plurality of infrared dongles is configured to communicate with the machine executable program of the computing device and the machine executable program of the healthcare management device and facilitate communication of the medical information generated by the medical device to the memory of the computing device.

* * * * *